US005705350A

United States Patent [19]
Mudryj et al.

[11] Patent Number: 5,705,350
[45] Date of Patent: Jan. 6, 1998

[54] TRANSCRIPTION FACTOR COMPLEXES IN SENESCENT CELLS

[75] Inventors: Maria Mudryj; Cynthia A. Afshari, both of Durham, N.C.

[73] Assignee: Duke University, Durham, N.C.

[21] Appl. No.: 520,753

[22] Filed: Aug. 29, 1995

[51] Int. Cl.⁶ .......................... C07K 14/435; C12Q 1/68; G01N 33/50; G01N 33/573
[52] U.S. Cl. .................. 435/7.21; 435/6; 435/7.4; 435/15; 435/194; 436/63; 436/86; 530/350; 530/358
[58] Field of Search ....................... 530/350, 358; 435/7.21, 7.4, 194, 6, 15; 436/63, 86, 6

[56] References Cited

U.S. PATENT DOCUMENTS

| | | | |
|---|---|---|---|
| 5,302,706 | 4/1994 | Smith | 536/23.1 |
| 5,384,255 | 1/1995 | Ciechanover et al. | 435/193 |
| 5,473,056 | 12/1995 | Ivey-Hoyle et al. | 530/358 |
| 5,491,069 | 2/1996 | Dirmi et al. | 435/195 |

FOREIGN PATENT DOCUMENTS

| | | |
|---|---|---|
| 2 282 814 | 4/1995 | United Kingdom. |
| WO 93/15227 | 8/1993 | WIPO. |
| WO 94/10307 | 5/1994 | WIPO. |

OTHER PUBLICATIONS

N. Dyson; pRB, p107 and the regulation of the E2F transcription factor, *J. Cell Science*, Supplement 18:81–87 (1994).

Y. Ziong et al.; p21 is a universal inhibitor of cyclin kinases, *Letters to Nature* 366:701–704 (1993).

*Primary Examiner*—David Saunders
*Attorney, Agent, or Firm*—Myers Bigel Sibley & Sajovec, L.L.P.

[57] ABSTRACT

A method of screening a cell for the onset of senescence or a senescent state therein comprises detecting a p21-E2F complex in the cell, an elevation in the complex as compared to a normal cell indicating the onset of senescence or a senescent state in the cell. Isolated complexes comprised of p21 and E2F are also disclosed. The complexes stably bind to DNA and are useful, among other things, for binding DNA.

23 Claims, 3 Drawing Sheets

FIG. 1

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear     ( i i ) MOLECULE TYPE: cDNA (x i) SEQUENCE DESCRIPTION: SEQ ID NO:1:

GCTAGCCATG GCAGAACCGG CTGGGGATGT                                30

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:2:

CTCGAGGATC CTTAGGGCTT CCTCTTGGAG                                30

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:3:

CCCAAGCTTA TGTCAGAACC GGCT                                     24

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:4:

GCTCTAGAGG ATTAGGGCTT CCTCTTG                                  27

TRANSCRIPTION FACTOR COMPLEXES IN SENESCENT CELLS

This invention was made with Government support under Merit Grant Number 0001 from the Veterans Administration. The Government has certain rights to this invention.

FIELD OF THE INVENTION

The present invention relates to methods of screening cells for the onset of senescence or a senescent state therein by detecting an E2F-p21 complex, and to E2F-p21 complexes.

BACKGROUND OF THE INVENTION

Normal cells in culture undergo a finite number of population doublings, after which both DNA replication and cellular division cease but metabolic activity and cellular viability are maintained for an extended period of time. In contrast, immortal cell lines established from tumors are capable of proliferating indefinitely. The loss of proliferative activity while maintaining cell viability is a hallmark of cellular senescence and an in vitro model of aging. See L. Hayflick, *N. Eng. J. Med.* 295, 1302–1308 (1976).

The ability of cells to progress through the cell cycle is primarily regulated by the sequential formation, activation, and subsequent inactivation, of a series of structurally related serine/threonine kinases, which consist of a catalytic subunit, a CDK (cyclin-dependent kinase), and a cyclin regulatory subunit. T. Hunter and J. Pines, *Cell* 79, 573–582 (1994); C. Sherr, *Cell* 79, 551–555 (1994). The enzymatic activity of a CDK is also regulated (predominantly negatively) by a number of small proteins that physically associate with cyclins, CDKs, or their complexes. In mammalian cells, there exist at least two distinct families of CDK inhibitors, represented by two prototype CDK inhibitors p21 and p16. T. Hunter and J. Pines, supra. One such cyclin-CDK interacting protein, p21, identified as a component of quaternary cyclin-CDK complexes that also contained PCNA [proliferating cell nuclear antigen, (Y. Xiong et al., *Cell* 71, 505–514 (1992); Y. Xiong et al., *Genes Dev.* 7, 1572–1583 (1993); H. Zhang et al., *Mol. Biol. Cell* 4, 897–906 (1993)], was recently found to be a potent inhibitor of all cyclin-CDK enzymes that have been examined (J. Harper, *Cell* 75, 805–816 (1993); L. Hayflick, *N. Engl. J. Med.* 295, 1302–1308 (1976); Y. Xiong et al., *Nature* 366, 701–704 (1993)). p21 was not only isolated through its physical interaction with cyclins and CDKs, but also as a gene whose transcription is induced by wild-type p53 function [WAF1, (W. El-Deity et al., *Cell* 75, 817–825 (1993))]. In addition, p21 was first isolated for its elevated expression in senescent cells Sdi1, (A. Noda et al., *Exp. Cell. Res.* 211, 90–98 (1994), See also J. Smith, U.S. Pat. No. 5,302,706). It has been proposed that the inhibition of cyclin/CDK activity by p21 may contribute the senescent phenotype (V. Dulic et al., *Proc. Natl. Acad. Sci. USA* 90, 11034–11038 (1993)).

Tumor suppressors, proteins that function in negative growth regulation, may also be involved in senescence. R. Weinberg, *Science* 254, 1138–1146 (1991). One mechanism by which Rb functions is through its interaction with the transcription factor E2F (S. Chellappan et al., *Cell* 65, 1053–1061 (1991); S. Hiebert et al., *Genes Dev.* 6, 177–185 (1992); J. Nevins, *Science* 258, 424–429 (1992); see also J. Nevins and S. Chellappan, PCT Patent Application WO 93/15227).

The E2F transcription factor family has been implicated in both the positive and negative regulation of growth promoting genes (L. Bandara et al., *EMBO J.* 12, 4317–4324 (1993); K. Helin et al., *Genes Dev.* 7, 1850–1861 (1993); H. Huber et al., *Proc. Natl. Acad. Sci. USA* 90, 3525–3529 (1993); J. Lees et al., *Mol. Cell. Biol.* 13, 7813–7825 (1993); see also A. Ciechanover et al., U.S. Pat. No. 5,384,255; M. Ivey-Hoyle et al., UK Patent Application 2 282 814A; N. LaThangue, PCT Patent Application WO 94/10307). E2F activates the transcription of several genes required for DNA synthesis, such as dihydrofolate reductase and thymidine kinase, that are down-regulated in growth arrested cells. Furthermore, E2F complexed with the unphosphorylated form of Rb negatively regulates transcription (S. Hiebert et al., *Genes Dev.* 6, 177–185 (1992); S. Weintraub et al., *Nature* 358, 259–261 (1992)). Recently it has been shown that overexpression of E2F1 in growth arrested cells can overcome this negative effect and cause cells to progress into DNA synthesis in the absence of additional stimuli. D. Johnson et al., *Nature* 365, 349–352 (1993); P. Singh et al., *EMBO J.* 13, 3329–3338 (1994).

SUMMARY OF THE INVENTION

We have identified four specific E2F complexes in aged and senescent cells. Two novel p21-containing E2F complexes were identified. One complex consisted essentially of Rb, p21, CDK2, and cyclin E, and the other complex consisted essentially of p107, p21, CDK2, and cyclin D1. The p21 containing complexes bound DNA approximately ten times more stably than other E2F complexes or uncomplexed E2F.

In view of the foregoing, a first aspect of the present invention is a method of screening a cell for the onset of senescence or a senescent state therein. The method comprises detecting a p21-E2F complex in the cell, an elevation in the complex as compared to a normal cell indicating the onset of senescence or a senescent state in the cell.

A second aspect of the present invention is an isolated complex of broteinaceous material containing p21 and E2F. Preferably, the complex further contains a CDK (e.g. CDK2), a cyclin (e.g., cyclin D1, cyclin E), Rb and/or p107. The complexes are useful, among other things, for binding DNA.

In addition, two of the four E2F complexes identified (an Rb-E2F and a G1-specific, putative p130-E2F) have been previously characterized in G0-arrested cells (D. Cobrinik et al., *Genes and Devel.* 7, 2392–2404 (1993): J. Schwarz et al., *EMBO J.* 12, 1013–1020 (1993)).

The foregoing and other objects and aspects of the present invention are set forth in detail in the drawings herein and the specification given below.

DETAILED DESCRIPTION OF THE INVENTION

The present invention may be carried out with any type of cells. Cells used to carry out the present invention are generally mammalian cells (e.g., dog, cat, rat, monkey, or human cells). Cells used to carry out the present invention may be of any type or tissue of origin, including., but not limited to, fibroblasts, epithelial cells, endothelial cells (e.g., vascular endothelial cells), blood cells (e.g., peripheral blood cells), etc. The cells may be obtained from any source, such as cells grown in an in vitro cell culture, cells obtained from a tissue sample, or cells obtained directly from an animal subject.

The term "senescence," as used herein, refers to the loss of proliferative ability, while maintaining viability, by a cell. The phrase "onset of senescence," as used herein, refers to cells which, though they retain some proliferative ability, have limited proliferative ability and are to enter a senescent state in the near future, after relatively few mitotic cycles (as compared to normal cells of the same type).

"p21" herein refers to the p21 protein, which is known (see, e.g., Y. Xiong, Nature 366, 701–704 (1993)), and was previously known as SDI1 (see U.S. Pat. No. 5,302,706 to Smith).

"E2F" herein refers to the E2F transcription factor, which is known. See, e.g., PCT Patent Application WO 93/15227. Any member of the E2F family may be employed in providing complexes of the present invention, including. E2F-1, E2F-2, E2F-3, and E2F-4. See, e.g., UK Patent Application GB 2282814A to M. Ivey Hoyle et al. Currently preferred is that E2F which is found in complexes isolated directly from cells containing complexes of the invention.

"CDK" herein refers to the group of enzymes known as cyclin dependent kinases, including CDK2, CDK3, CDK4, and CDK5. The CDKs are known. See, e.g., C. Sherr, Cell 73, 1059–1065 (1993). "Cyclin" herein refers to a regulatory subunit of the CDKs, and includes Cyclins A to E. See C. Sherr, supra. CDK2, Cyclin D1 and Cyclin E, which are found in complexes isolated from cells containing complexes of the invention, are currently preferred.

"Rb" refers to the protein product of the retinoblastoma susceptibility gene (RB1), which is known. See, e.g., PCT Patent Application WO 93/15227.

"p107" refers to a protein related to, but distinct from, Rb. See, e.g., Ewen MC et al., Cell 66:1155 (1991).

The E2F, p21, CDK, cyclin, Rb, and p107 proteins may be of any species of origin, but are preferably mammalian (e.g., dog, cat, rat, mouse, monkey, human) in origin. Preferably, all proteins in the complex are of the same species.

Complexes of the present invention may be obtained from senescent cells of the foregoing types in accordance with standard isolation and purification techniques, as will be apparent to those skilled in the art in light of the Examples given below. For example, senescent cells may be lysed and the complexes isolated from the cell lysate by affinity purification (e.g., immobilized antibody, immobilized DNA) in accordance with known techniques. Alternatively, the component parts of the complexes may be obtained separately and combined together in an aqueous solution (e.g., a phosphate-buffered saline solution) to form the isolated complexes in vitro. Currently, it is preferred that complexes of the invention are isolated directly from cells containing the complexes.

As noted above, the present invention provides a method useful as an aid to determining the onset of senescence or a senescent state in cells. In general, the method comprises first collecting a sample containing a p21-E2F complex from the cells, and then determining the presence or absence of an elevation in the complex as compared to normal cells, with an elevation in the complex as compared to normal cells indicating the onset of senescence or a senescent state in the cells. In carrying out the method, the presence and amount of the complexes may be detected and determined by any suitable means, including immunoassay, affinity binding assay, and gel retardation assay, in accordance with known techniques. See, e.g., PCT Patent Application WO93/15227. The complex may be collected from the cells by lysing the cells, also in accordance with known techniques.

The method of the present invention is useful in a variety of different applications. For example, the methods of the present invention may be utilized to evaluate the suitability of cells that have been grown in culture for further use, where it would be undesirable to use senescent cells or cells at the onset of senescence in a further application (e.g., an industrial fermentation process). The methods of the present invention may also be utilized to evaluate the suitability of cells collected from an animal subject for subsequent growth in culture, where it would be undesirable to use senescent cells or cells at the onset of senescence in the further application (e.g., an industrial fermentation process). The methods of the present invention may also be utilized to evaluate the suitability of cells obtained from a subject for subsequent therapeutic treatment, or provide an indication of the regenerative capacity of cells (i.e., provide an indication of wound healing capacity).

The complexes of the present invention also are useful in a variety of different applications. Because of their high binding affinity for DNA, the complexes may be immobilized on a solid support such as sepharose (e.g., by first immobilizing on the solid support an antibody that selectively binds to a constituent of the complex in accordance with standard techniques, and then binding the complex to the immobilized antibody by contacting an aqueous solution containing the complex to the immobilized antibody), and the immobilized complexes used to isolate and/or purify DNA from a solution. The complexes may be provided in an aqueous solution (particularly, a pharmaceutically acceptable solution such as sterile pyrogen-free physiological saline solution) and administered to a suitable animal (e.g., rabbit, horse) for the purpose of producing antibodies thereto, which antibodies may be collected from the animal and used in immunoassays in the methods described above. The complexes may be provided in an aqueous solution and used in screening methods to identify agents, either naturally occurring or synthetic, that disrupt or promote complex formation. Agents that disrupt complex formation would be of interest as candidate compounds for inhibiting senescence in cells, would be useful in carrying out industrial fermentation processes, and would be useful in treating or facilitating wound healing. Agents that facilitate complex formation would be of interest as candidate compounds for facilitating senescence in cells, and would be useful in treating or inhibiting uncontrolled cell growth in oncogenically transformed cells.

In the following Examples, "PMSF" means phenylmethylsulfonyl fluoride, "SAP" means serine aspartate pyruvate solution, "h" means hours, "min" means minutes, "µCi" means microcuries, "ml" means milliliters, "µl" means microliters, "PBS" means phosphate buffered saline, "rpm" means revolutions per minute, and temperatures are given in degrees centigrade unless otherwise indicated.

EXAMPLE 1

Cell Lines and Culture Conditions

Normal human lung, diploid fibroblasts, (WI38) passage 13, were obtained from the American Type Culture Collection (ATCC, Rockville Md.). Cells were cultured at 37° C. in Dulbecco's modified Eagle's medium supplemented with 10% fetal calf serum and SAP (0.2 mM serine, 0.1 mM aspartate, 1 mM pyruvate) and were passaged at a 1:5 split ratio until doubling times began to increase; then cells were passaged 1:3 and ultimately 1:2. Senescent cell cultures were maintained at no more than 50% confluence and were refed twice weekly with fresh medium. Cells were stimulated with fresh medium 24 h prior to harvesting for cell extracts. For growth arrest of young cells, cells were grown to approximately 70% confluence and then starved for 48 h in medium containing 0.5% serum. Cells were designated as aged or senescent when the 48 h labeling indices were less than 20 and 3%, respectively.

EXAMPLE 2

Autoradiography of Cells

For cell labeling experiments, cells were plated at the same density as cells that were plated for cell extracts. Labeling was started 48 h prior to harvest by the addition of fresh medium containing 2 µCi/ml $^3$H-thymidine. After a 48 h labeling period, cells were rinsed twice with phosphate buffered saline (PBS), fixed with 50% methanol:acetic acid (4:1) for 15 min., followed by fixing in methanol:acetic acid (4:1) for an additional 15 min. Dishes were rinsed with $H_2O$, coated with NTB-2 bulk emulsion (Kodak), stored at 4° C. for 4 days, then developed and fixed. The percent labeling index (%LI) was scored as the number of labeled nuclei/total number of nuclei, and at least 500–1000 nuclei were scored per dish.

EXAMPLE 3

Gel Shift Assays

Whole cell extracts for gel shift analysis were prepared in accordance with known procedures. See M. Mudryj et al., Cell 65, 1243–1253 (1991). However, after rinsing cells twice with cold PBS, cells were scraped and pelleted. Excess PBS was removed and cell pellets were frozen at −80° C. Prior to the extraction, cold lysis buffer (containing the protease inhibitors PMSF, leupeptin, Pefabloc, aprotinin, and pepstatin, and the phosphatase inhibitors, sodium fluoride, and sodium orthovanadate, see M. Mudryj et al., supra), was added on top of each frozen pellet and the cell pellet was thawed on ice in the presence of these inhibitors. Failure to do this with aged and senescent cell pellets resulted in degradation of proteins. Extracts and gel shift assays were performed as described previously. See M. Mudryj et al., supra. Competitions were performed using 100-fold excess cold probe, and off-rate experiments were conducted by adding cold competitor to a binding reaction after the reaction reached equilibrium (20 min. at room temperature). Aliquots of the mixture were applied to a gel that was already running at time points after the addition of competitor.

EXAMPLE 4

Immunoprecipitation of E2F Associated Binding Activity

For immunoprecipitation of whole cell extracts, 50 µg of protein was precleared by the addition of either 30 µl of protein A or protein G-sepharose for 1 hour. Beads were pelleted and supernatant was transferred to a new tube containing antibody. Rb and p53 antibodies were from Oncogene Science Inc. Rabbit polyclonal antibodies specific to human CDK2 and cyclin D1 were from Upstate Biotechnology, Inc. or as previously described (Xiong Y. et al., Cell 71:505 (1992)), both have been characterized for their ability to coimmunoprecipitate associated cellular proteins. Following antibody binding (16 h), protein A or protein G-sepharose beads were added for 1 h and washed 4 times with 1X gel shift buffer (Mudryj M. et al., Cell 65:1243 (1991)) containing 3 µg/ml BSA. Beads were resuspended in 5 µl of shift buffer and 0.5 µl of 8% deoxycholate was added to dissociate complexes (10 min. at room temperature). The supernatant was removed, 2 µl of 10% NP40 was added, and the entire supernatant was assayed for the presence of E2F by E2F gel shift analysis as described previously (M. Mudryj et al., supra). For histone kinase assays, immunoprecipitated proteins were incubated with gamma-$^{32}$P ATP and histone as previously described (S. Devoto et al., Cell 68, 167–176 (1992)).

EXAMPLE 5

Glycerol Gradient of Senescent Cell Extract

Senescent cell extracts (2 mg) were concentrated four fold by ammonium sulfate precipitation at 4° C. Concentrated cell extract was then loaded above a 5 ml 5–25% glycerol gradient that contained protease inhibitors. The gradient was centrifuged at 40,000 rpm for 18 h. A 26 gauge needle was used to puncture the bottom of the tube and 3 drop fractions were collected (flow rate=1 drop/1 min. 20 sec.) for the first thirty fractions or approximately half of the gradient. The remaining gradient was collected in about 15 drop fractions. The gradient was assayed by mixing 5 µl of every other fraction in an E2F gel shift reaction and assayed as described above.

EXAMPLE 6 p21 Protein Purification, Activity Assay and Antibody

To express the human p21 gene in bacteria, a T7-p21 expression plasmid was constructed by amplifying the isolated human p21 cDNA clone (Y. Xiong et al., Nature 366, 701–704 (1993)) using PCR with the following primers: 5'GCTAGCCATG GCAGAACCGG CTGGGGATGT 3' (SEQ ID NO:1) and 5'CTCGAGGATC CTTAGGGCTT CCTCTTGGAG 3' (SEQ ID NO:2). The 500 bp PCR product containing the full length of the p21 coding region was subcloned into a T7 expression vector (pET3d, 48). After the last step of a sizing column, p21 protein was purified to near homogeneity as determined by Coomassie Blue staining, as is known in the art. To assay the inhibitory activity of purified p21 protein, equal amounts of cell extract, derived from human 293 or Li-Fraumeni cells that do not express detectable levels of p21 mRNA or protein, were preincubated with variable amounts of p21 protein prior to the immunoprecipitation with an antibody specific to a cyclin or CDK. The anti-cyclin or anti-CDK immunoprecipitates were assayed for kinase activity using an excess of Hi as a substrate (2 μg H1/60 μl reaction). p21 protein purified from bacteria was found to quantitatively inhibit the kinase activity on a variety of cyclin and CDK proteins including CDC2, CDK2, cyclin A and cyclin B1.

Generation of a rabbit polyclonal anti-p21 antibody was as described previously (Y. Li, *Oncogene* 9, 2261–2268 (1994)). This antibody appears to recognize a conformation specific epitope as determined by methionine metabolic labeling and immunoblotting. This antibody can recognize p21 protein present in a variety of cyclin and CDK complexes as demonstrated by its ability to co-immunoprecipitate a number of cyclins, CDKs, and PCNA with p21 in addition to its ability to co-immunoprecipitate E2F-associated DNA binding activity.

EXAMPLE 7

E2F-mediated transfection assay $2 \times 10^5$ NIH 3T3 cells were plated per dish. The following day, cells were re-fed and transfected overnight with 15 μg each of plasmid DNA [5 μg of appropriate plasmids were used and adjusted to 15 μg total by the addition of excess pRcCMV (InVitrogen)] plus 5 μg of either E2-CAT (chloramphenicol acetyl-transferase) or a mutant E2-CAT plasmid by the calcium phosphate transfection method (S. Lester et al., *Somat. Cell Genet.* 6, 241–259 (1980); M. Wigler et al., *Cell* 14, 725–731 (1978)). The next day, cells were washed with serum free medium and re-fed with fresh medium containing 10% calf serum. Two days after transfection, cells were harvested, normalized for protein concentration, and assayed for CAT activity as previously described (C. Gorman et al., *Mol. Cell. Biol.* 2, 1044–1051 (1982)). Radioactive counts were quantitated both by phosphorimager analysis and liquid scintillation counting.

EXAMPLE 8 p21 Expression Plasmid

Two pCMV-p21 expression plasmids were used in transfections. One pCMV-p21 plasmid was constructed by amplifying the human p21 cDNA by coupled reverse transcription and polymerase chain reaction (RT-PCR) of senescent cell mRNA using the following primers: 5'CCCAAGCTTA TGTCAGAACC GGCT 3' (SEQ ID NO:3) and 5'GCTCTA-GAGG ATTAGGGCTT CCTCTTG 3'(SEQ ID NO:4). The purified PCR product was verified by sequencing and digested with HindIII and XbaI, and cloned into pRcCMV (InVitrogen). The other pCMV-p21 plasmid has been previously shown to inhibit cell proliferation (Y. Xiong, *Nature* 366, 701–704 (1993)). Both expression plasmids showed similar activity in repressing E2F-dependent transcription and the first expression plasmid was used throughout this work.

EXAMPLE 9

New E2F Complexes Are Present in Senescent Normal Human Fibroblasts

In order to study changes in E2F complex composition during cellular aging, extracts were prepared from cells at various stages of in vitro aging. As the generation time of the cell cultures increased and the proliferative potential decreased, slow migrating E2F complexes became abundant. The extracts from the serum-stimulated, aged cultures contained four E2F complexes which were specific for binding to an E2F DNA binding site. One of these four complexes resembled the previously identified G1-specific p130-E2F complex (D. Cobrinik et al., *Genes and Devel.* 7, 2392–2404 (1993)) while another was identified, using supershift analysis with a Rb antibody, to the previously reported Rb-E2F complex (S. Chellappan et al, *Cell* 65, 1053–1061 (1991)). The doublet containing the remaining two unidentified complexes could be supershifted with Rb and p107 antibodies. The slowly migrating complexes in the aged cell extracts appeared to be identical but more abundant than the complexes present during G1 in the young cell extracts. For comparison young fibroblasts were arrested in G0 by serum deprivation and induced to enter the cell cycle by serum addition. Cells were harvested and extracts were prepared at various times after serum addition. Gel shift analysis of E2F complexes in young cells showed two G1-E2F complexes, the Rb-E2F and the putative G1-specific, p130-containing E2F that have been previously described (S. Chellappan et al., supra, D. Cobrinik et al., supra; J. Schwarz et al., *EMBO J.* 12, 1013–1020 (1993)). In addition, the complex containing the cyclin A/CDK2-p107 E2F complex which was designated the S-phase complex (S. Devoto et al., *Cell* 68, 167–176 (1992); E. Lees et al., *Genes Dev.* 6, 1874–1885 (1992); and M. Mudryj et al., *Cell* 65, 1243–1253 (1991)), was observed to increase in late G1 as the putative p130, G1-specific complex disappeared. The Rb complex persisted through S-phase as described previously (Id.). However, in addition there was a faint doublet that had a slower mobility than the S-phase complex that appeared to increase throughout G1 and to disappear upon formation of the S-phase, cyclin A complex in late G1. It is this doublet that increased in amount as cells aged in culture. We also observed the same high level of the novel complexes in senescent human foreskin fibroblasts (M190 cells). Experiments to identify the protein components present in these novel E2F complexes are described below.

EXAMPLE 10

Novel E2F Complexes Contain the p21 Protein

Previous studies have shown that E2F can complex with CDK2 and cyclins A and E (Id.). Since the levels of p21, CDK2, and cyclins D and E are elevated during senescence (V. Dulic et al., *Cell* 76, 1013–1023 (1994); F. Lucibello et al., *J. Cell Sci.* 105, 123–133 (1993); and A. Noda et al., *Exp. Cell Res.* 211, 90–98 (1994)) as well as during G1 (T. Hunter and J. Pines, *Cell* 79, 573–582 (1994); Y. Li et al., *Oncogene* 9, 2261–2268 (1994); and C. Sherr, *Cell* 79, 551–555 (1994)) we investigated the possibility that p21 could be a component of the slowly migrating E2F complexes through a cyclin/CDK interaction.

Immunoprecipitation of senescent cell, G1 and S-phase extracts with p21 antibodies, followed by dissociation of the complexes and an assay for E2F binding showed that p21 was associated with E2F in senescent cells. p21 was also associated with E2F in young G1 synchronized cells but not during S-phase, showing a specificity of the p21-E2F interaction only during G1 and senescence. Immunoprecipitation with an Rb antibody served as a positive control since the Rb-E2F complex was present in all three extracts. The p21-E2F association was specific since preincubation of the antibody with purified p21 protein failed to precipitate any E2F-associated activity. Cyclins D and E and CDK2 were also associated with E2F in extracts from senescent and young G1 cells.

Figure 1:
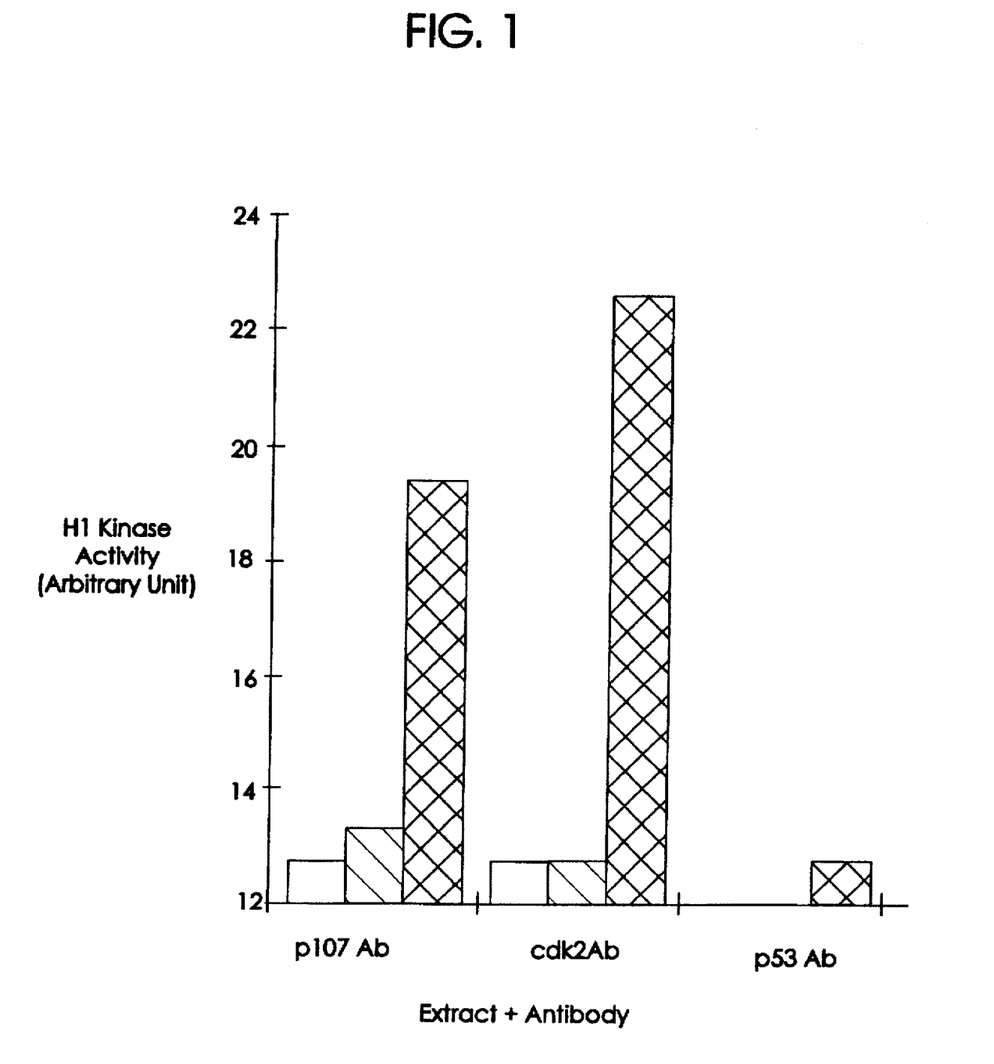
FIG. 1 shows histone kinase activity in p107 and cdk2 immunoprecipitates from S-phase (solid bars) and G1 (shaded bars) extracts from young cells as well as extracts from senescent cells (open bars). Counts were quantitated by phosphoimager analysis.

To address the function of the cyclin/CDK2 interaction associated with E2F, the ability of these complexes to phosphorylate histone was examined (FIG. 1). p107 and CDK2 immunocomplexes precipitated from young S-phase cells had high histone kinase activity as previously shown (S. Devoto et al., *Cell* 68, 167–176 (1992)), but p107 and CDK2 immunoprecipitates from senescent and young G1-arrested cells had very low kinase activity, indicating that CDK2 was present in an inactive form in these E2F complexes. p21-containing CDK complexes can be both catalytically active and inactive, dependent on the stoichiometry. H. Zhang et al., *Genes and Dev.* 8, 1750–1758 (1994).

We could not definitively identify p21 in any of the E2F complexes by supershift analysis. Therefore, in order to identify the proteins present in each specific complex, and the complexes that contained p21, senescent cell extract was fractionated over a glycerol gradient and assayed for E2F binding activity. Glycerol gradient fractionation was established as a purification/isolation protocol in the identification of the cyclin A-E2F complex. M. Mudryj et al., *Cell* 65, 1243–1253 (1991). Fractions homogeneous for specific complexes were pooled, immunoprecipitated with specific antibodies, and assayed for E2F binding activity. Fractions 12–26 contained the slowest mobility, novel E2F-binding complex and contained p21, cyclin E, CDK2 and Rb. The pool of fractions 36–40 contained the other new E2F complex that contained p21, cyclin D, CDK2, and the p107 protein. The specific bands in these immunoprecipitations were quantitated by densitometry scanning and quantitated to range for example, from 6.2-fold to 90-fold elevation over background bead controls for cyclin E and p107, respectively. The complex in fractions 46–50 had the same electrophoretic mobility as the previously identified Rb-E2F complex and did not contain cyclin D or CDK2 confirming previous postulates. M. Ewen et al., *Cell* 73, 487–497 (1993). Antibodies to p21, cyclin D, p107, and Rb did not co-precipitate E2F from fractions 27–35, indicating that these proteins are not components of the G1-specific, putative p130-E2F complex.

In summary, two novel E2F complexes were identified in aged and senescent normal human fibroblasts, one containing p21, cyclin D1, CDK2, and p107, and the other containing p21, cyclin E, CDK2, and Rb. We did not observe these new, p21-containing E2F complexes in several transformed lines examined including Li-Fraumeni cells which do not contain detectable levels of p21. Y. Li et al., *Oncogene* 9, 2261–2268 (1994).

EXAMPLE 11 p21 Containing E2F Complexes Bind DNA Through a Stable Interaction

One way that p21 could modulate the expression of E2F regulated genes would be by altering the DNA binding affinity of the E2F complexes. Previous studies have shown that E2F binding to the adenovirus E2 as well as the DHFR promoter is unstable. S. Neill and J. Nevins, *J. Virol.* 65, 5364–5373 (1991); S. Obert et al., Hearing, *Mol. Cell. Biol.* 14, 1333–13346 (1994); and M. Wade et al., *J. Biol. Chem.* (in press) (1995). To determine the binding stability of the various complexes, senescent, young G1 and S phase extracts were analyzed in off-rate experiments. The binding of the Rb, G1 and S phase complexes was unstable, because binding was virtually abolished within five minutes after addition of competitor. The p21 containing complexes, however, bound DNA more stably. Analysis of the senescent extract showed that twenty minutes after the addition of competitor, only the p21 containing complexes remained. Densitometric analysis indicated that while the half-life of binding of the Rb, G1 and S phase complexes to DNA was less than two minutes [consistent with previous studies: S. Neill and J. Nevins, *J. Virol.* 65, 5364–5373 (1991); S. Obert et al., *Mol. Cell. Biol.* 14, 1333–13346 (1994); and M. Wade et al., *J. Biol. Chem.* (in press 1995)], the half-life of the p21 containing complexes was approximately 17 minutes. By significantly enhancing the binding stability of E2F complexes, p21 may modulate the expression of E2F dependent genes.

EXAMPLE 12 p21 Functions to Inhibit Transcription Through E2F

Figure 2:
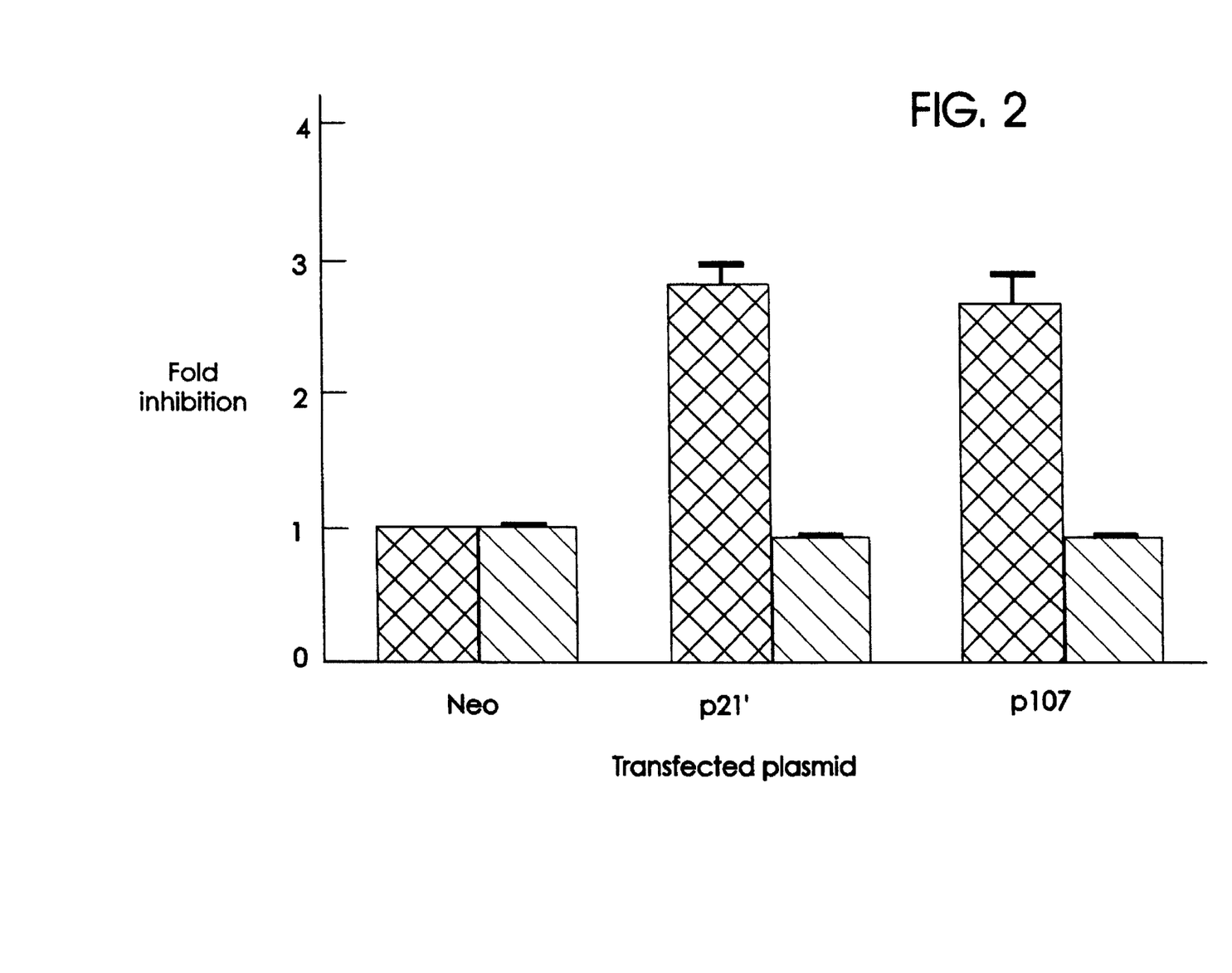
FIG. 2 shows the results of transient transfection assays of NIH3T3 cells. Cells were co-transfected with E2-wild-type (solid bars) or E2-mutant (shaded bars)-CAT plasmids in the presence or absence of 5 µg of pRcCMV, CMV-p21, or CMV-p107 expression plasmids. Extracts were prepared 48 hours after transfection and assayed for CAT activity. Fold inhibition is expressed as the amount of $^{14}C$ cpm acetylated chloramphenicol for neo control divided by the amount in p21 or p107 transfections.

To determine the potential effect of p21 on E2F dependent transcription, a CAT reporter plasmid containing wild type or mutant E2 promoter that can no longer be recognized by E2F was co-transfected into NIH3T3 cells with pCMV-neo, and p21 (pCMV-p21), p107 (pCMV107) overexpression plasmids. As shown in FIG. 2, the co-expression of p21 inhibited transcription from the wild-type promotor by three-fold over the neo control. As previously reported, CMV-p107 also had an inhibitory effect on E2F-dependent transcription (2.8-fold inhibition). J. Schwarts et al., *EMBO J.* 12, 1013–1020 (1993); L. Zhu et al., *Genes Dev.* 7, 1111–1125 (1993). The level of inhibition by p21 is similar to what has been reported for both Rb and p107. S. Hiebert et al., *Genes Dev.* 6, 177–185 (1992); J. Schwarz et al., *EMBO J.* 12, 1013–1020 (1993). The levels of transcription from a mutant E2 promoter that does not bind E2F, were not altered by any of the proteins indicating a specificity for the inhibitory effect of p21 and p107. S. E2F-dependent transcription.

EXAMPLE 13

The Cyclin A/CDK2-p107-E2F S-Phase Complex is Dissociated by p21

It appeared that during senescence p21 interacted with E2F by binding specific complexes that subsequently inhibited transcription. Additional experiments utilizing purified p21 protein suggested that p21 had another distinct activity that regulated E2., p21 protein was expressed and purified from bacteria. This protein inhibited the histone H1 kinase activity of various cyclin-CDK enzymes including cyclin A and CDC2 in cell extracts. The addition of this purified p21 protein to a glycerol gradient purified S phase complex increased the mobility of the complex. The amount of in vitro made p21 used in these experiments was within the range used in other reports investigating p21 function. Y. Gu et al., *Nature* 366, 707–710 (1993); J. Harper et al., *Cell* 75, 805–816 (1993); S. Waga et al., *Nature* 369, 574–578 (1994); Y. Xiong et al., *Nature* 366, 701–704 (1993). The Rb-E2F complex was unaffected by p21. The putative p130 G1 complex, as well as the senescent p21 containing complexes, were also unaffected. As previously described (S. Devoto et al., *Cell* 68, 167–176 (1992); E. Lees et al., *Genes Dev.* 6, 1874–1885 (1992)), the addition of p107, cyclin A and CDK2 antibodies to gel shift reactions containing the S-phase E2F complex caused a supershift of the S-phase band indicating that all three proteins were components of this complex. However, addition of these antibodies to an S-phase complex that had been altered by the addition of purified p21 protein only showed a supershift with the addition of the p107 antibody, and was no longer supershifted with the cyclin A and CDK2 antibodies. This strongly suggests that the addition of p21 to the S-phase complex caused the dissociation of cyclin A and CDK2 away from the p107-E2F components of the S-phase complex while not affecting the Rb-E2F complex. The lack of effect on the Rb complex is consistent with the absence of a cyclin and CDK in this complex. The addition of bacterially expressed purified cyclin D protein served as a control and did not affect any complexes. Thus, the p21 protein appeared to specifically dissociate the S-phase cyclin A/CDK2/p107-E2F complex, most likely through targeting the cyclin A and CDK2 proteins in the complex.

EXAMPLE 14 p21 May Mediate Senescence-Arrest Through An E2F Interaction

Without wishing to be bound to any particular theory for the instant invention, the following is provided as a possible mechanism underlying the observed interactions.

The S-phase, cyclin A/CDK2-p107-E2F complex and the new p21-containing E2F complexes are not present at the Same time. In young cells the cyclin A/E2F complex is present during S phase, the phase where p21 is downregulated. Since the half-life of the p21 protein is approximately 30 minutes (Y. Xiong, unpublished results) the level of protein would rapidly drop after transcription from the p21 gene is downregulated. Absence of p21-cyclin A/CDK2/p107/E2F interaction, as well as absence of the p21/E2F complexes, in young cells during this point in cell cycle can be simply the result of downregulation of p21 during S phase. This suggests another potential function of p21 in regulating cell cycle. Activation of p21 during S phase by triggers such as DNA damage could have three ways to halt cell cycle progression; 1. inhibit CDK kinase activity, 2. inhibit PCNA-dependent DNA replication, 3. dissociate cyclin A-CDK2 from E2F-p107 complexes.

Figure 3:
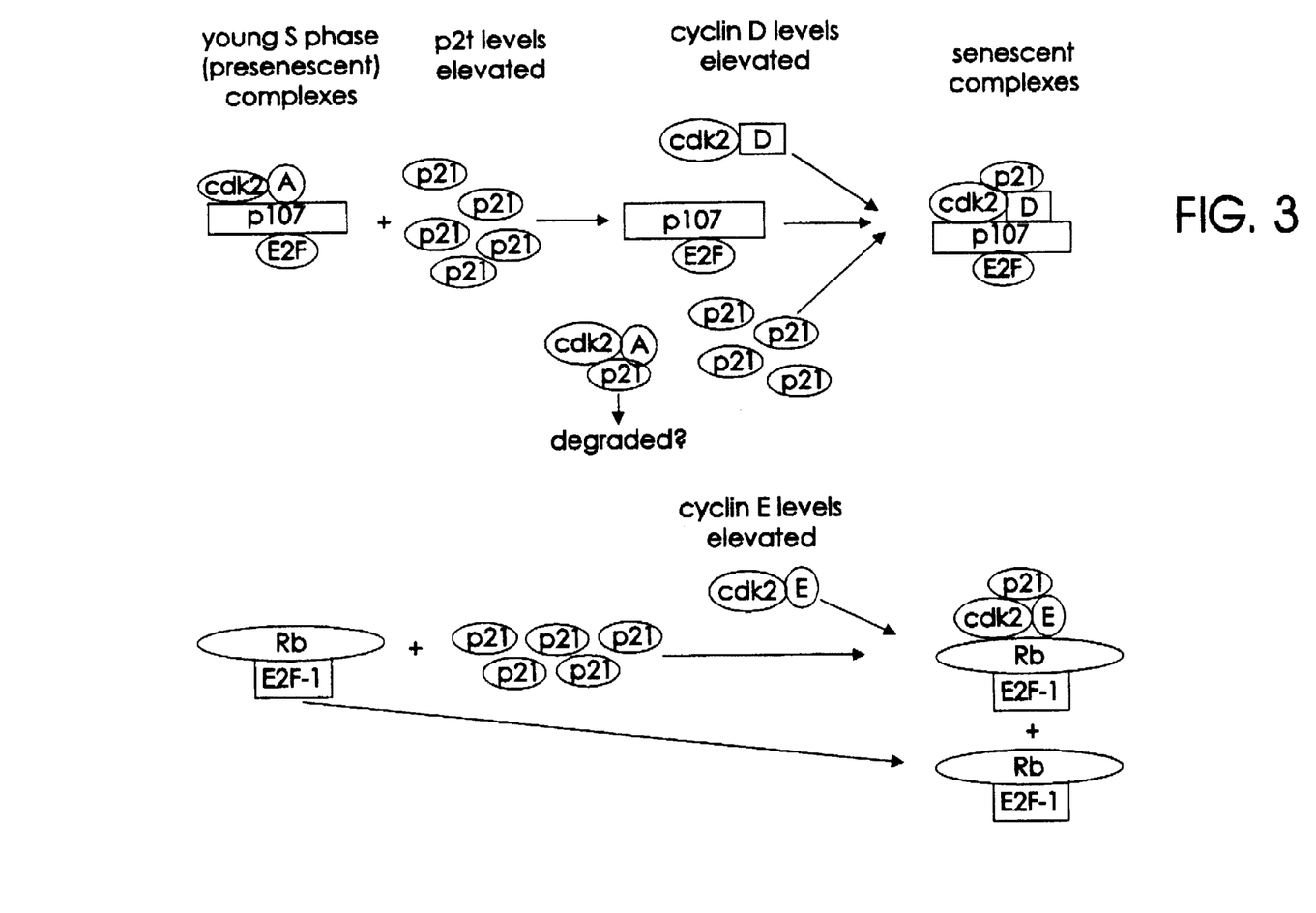
FIG. 3 illustrates a Model in which p21 dissociation of the S-phase cyclin A complex and the elevation of Cyclin D and Cyclin E levels may be instrumental in the formation of new E2F complexes during senescence.

Since recombinant p21 protein dissociates the cyclin A/CDK2 components from the E2F complex we propose that this is the initial event that leads to the assembly of p21 containing E2F complexes found in senescent cells. As depicted in FIG. 3, when p21 levels are elevated as cells age (A. Noda et al., *Exp. Cell. Res.* 211, 90–98 (1994)), cyclin A and CDK2 are dissociated by p21, leaving a p107-E2F protein complex, therefore altering the activity of this S-phase-E2F complex. In addition, cyclin E, cyclin D, and CDK2 levels also become elevated in G1 arrest and as cells age. V. Dulic et al., *Proc. Natl. Acad. Sci. USA* 90, 11034–11038 (1993); F. Lucibello et al., *J. Cell Sci.* 105, 123–b 133 (1993). Therefore, the p107-E2F complex, generated by p21 dissociation of the cyclin A/CDK2-p107 E2F complex, would be available to form a complex with cyclin D (FIG. 3). Similarly, the elevated levels of cyclin E would facilitate the formation of a new Rb-cyclin E-CDK2-p21-E2F complex (FIG. 3).

We have shown that in transient transfection assays that p21, similarly to p107 and Rb, downregulated E2F-mediated transcription. S. Hiebert et al., *Genes Dev.* 6, 177–185 (1992); J. Schwarz et al., *EMBO J.* 12, 1013–1020 (1993); L. Zhu et al., *Genes Dev.* 7, 1111–1125 (1993). There are several interpretations to explain these results. 1. The elevation of p21 would result in the inhibition of CDK kinases, the Rb protein would not be phosphorylated and would remain complexed with E2F, therefore E2F would act as a transcriptional repressor of growth promoting genes, 2. The elevation of p21, as well as cyclins D and E would result in the formation of p21-E2F complexes, complexes that bind DNA more stably then Rb/E2F, p107/E2F or p130E2F. Alteration of DNA binding stability of E2F by interaction with another protein has been previously demonstrated H, Huber et al., *J. Biol. Chem.* 269, 6999–7005 (1994). In vitro experiments have shown that the binding of Rb to E2F significantly increases the half-life of the complex H. Huber et al., supra. Recently, Wade et al. (*J. Biol. Chem.* in press 1995) have demonstrated that binding of E2F to a DHFR inverted repeat sequence that is present in the DHFR promoter is more stable than binding to a mutated site that preserves a single consensus E2F. This mutation in the DHFR inverted repeat decreases transcription from the promoter in in vitro, as well as in transient transfection assays. Taken together these data strongly suggest that alteration of binding stability is a potent regulatory mechanism for regulating E2F mediated gene expression. The presence of transcriptional repressors that tightly bind DNA would ensure that E2F dependent promoters such as DHFR, cdc2, or thymidine kinase remain transcriptionally repressed. Thus, in the absence of the transcription of genes critical for entry into S phase, the cell would remain permanently arrested in G1.

In conclusion, the p21 protein can regulate the cell cycle, as well as exit from the cell cycle by a number of distinct mechanisms: (1) inhibiting kinase activity of most, if not all CDKs, (2) inhibiting PCNA-dependent DNA replication, (3) blocking CDK phosphorylation and activation by CDK-activating kinase (CAK), and (4) regulating the activity of E2F.

The foregoing examples are illustrative of the present invention, and are not to be construed as limiting thereof. The invention is defined by the following claims, with equivalents of the claims to be included therein.

That which is claimed is:

1. A method of screening a cell for the onset of senescence or a senescent state therein, said method comprising:
   detecting a p21-E2F complex in said cell;
   an elevation in said complex as compared to a normal cell indicating the onset of senescence or a senescent state in said cell.

2. A method according to claim 1, wherein said cell is a mammalian cell.

3. A method according to claim 1, wherein said cell is a fibroblast cell.

4. A method according to claim 1, wherein said cell is an endothelial cell.

5. A method according to claim 1, wherein said cell is a vascular endothelial cell.

6. A method according to claim 1, wherein said cell is an epithelial cell.

7. A method according to claim 1, wherein said cell is a blood cell.

8. A method according to claim 1, wherein said detecting step is carried out by an assay selected from the group consisting of immunoassay, affinity binding assay, and gel retardation assay.

9. A method according to claim 1, wherein said detecting step is carried out by immunoassay.

10. A method useful as an aid to determining the onset of senescence or a senescent state in cells, said method comprising:
    collecting a sample containing a p21-E2F complex from said cells; and
    determining the presence or absence of an elevation in said complex as compared to normal cells;
    an elevation in said complex as compared to normal calls indicating the onset of senescence or a senescent state in said cells.

11. A method according to claim 10, wherein said determining step is carried out by an assay selected from the group consisting of immunoassay, affinity binding assay, and gel retardation assay.

12. An isolated complex of proteinaceous material comprising p21 and E2F.

13. An isolated complex according to claim 12, said complex further comprising CDK.

14. An isolated complex according to claim 13, said complex further comprising Rb.

15. An isolated complex of proteinaceous material comprising p21, E2F, CDK, Rb and cyclin E.

16. An isolated complex according to claim 13, said complex further comprising p107.

17. An isolated complex of proteinaceous material comprising p21, E2F, CDK, p107 and cyclin D1.

18. An isolated complex of proteinaceous material selected from the group consisting of:
   a complex comprised of p21, E2F, CDK2, Rb, and cyclin E; and
   a complex comprised of p21, E2F, CDK2, p107, and cyclin D1.

19. An isolated complex according to claim 12 immobilized on a solid support.

20. An isolated complex according to claim 12 in an aqueous solution.

21. A complex of proteinaceous material, useful as a marker for cell senescence, said complex isolated from a cell and comprising at least p21 and E2F.

22. A method of screening a cell for the onset of senescence or a senescent state therein, said method comprising:
   detecting a complex comprised of p21, E2F, CDK2, Rb, and cyclin E in said cell;
   an elevation in said complex as compared to a normal cell indicating the onset of senescence or a senescent state in said cell.

23. A method of screening a cell for the onset of senescence or a senescent state therein, said method comprising:
   detecting a complex comprised of p21, E2F, CDK2, p107, and cyclin D1 in said cell;
   an elevation in said complex as compared to a normal cell indicating the onset of senescence or a senescent state in said cell.

* * * * *